United States Patent
Bartholomew

(10) Patent No.: US 6,929,766 B2
(45) Date of Patent: Aug. 16, 2005

(54) DISPENSE MOLDING METHOD AND APPARATUS FOR MANUFACTURING CANNULAE

(75) Inventor: Ross Bartholomew, Orem, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 355 days.

(21) Appl. No.: 10/211,483

(22) Filed: Aug. 2, 2002

(65) Prior Publication Data

US 2003/0230823 A1 Dec. 18, 2003

Related U.S. Application Data

(63) Continuation-in-part of application No. 10/172,668, filed on Jun. 14, 2002.

(51) Int. Cl.⁷ .......................... B29C 41/08; B28B 1/38; B28B 1/32; B28B 1/02
(52) U.S. Cl. ...................... 264/294; 264/301; 264/303; 264/309; 264/310
(58) Field of Search ............................... 264/294, 301, 264/303, 309, 310

(56) References Cited

U.S. PATENT DOCUMENTS

| | | |
|---|---|---|
| 1,947,990 A | 2/1934 | Hopkinson |
| 2,081,533 A | 5/1937 | Ford et al. |
| 3,009,209 A | 11/1961 | Weinbrenner et al. |
| 3,412,431 A | 11/1968 | Lemelson |
| 3,802,908 A | 4/1974 | Emmons |
| 4,826,423 A | 5/1989 | Kemp et al. |
| 5,116,652 A | 5/1992 | Alzner |
| 5,496,294 A | 3/1996 | Hergenrother et al. |
| 5,537,729 A | 7/1996 | Kolobow |
| 5,630,806 A | 5/1997 | Inagaki et al. |
| 5,722,395 A | 3/1998 | Kolobow |
| 5,785,998 A | 7/1998 | Kolobow |
| 5,863,366 A | 1/1999 | Snow |
| 5,879,342 A | 3/1999 | Kelley |
| 5,885,251 A | 3/1999 | Luther |
| 5,947,940 A | 9/1999 | Beisel |
| 6,004,310 A | 12/1999 | Bardsley et al. |
| 6,030,371 A | 2/2000 | Pursley |
| 6,053,903 A | 4/2000 | Samson |

Primary Examiner—Stephen J. Lechert, Jr.
(74) Attorney, Agent, or Firm—Edwards Lifesciences

(57) ABSTRACT

A method of making a cannula utilizing dispense molding includes providing at least one dispense nozzle that dispenses a polymer material, providing a mandrel, moving at least one of the mandrel and at least one dispense nozzle relative to one another to produce an alternating pattern of polymer material along a longitudinal axis of the mandrel to form a tubular structure, and removing the tubular structure from the mandrel.

16 Claims, 7 Drawing Sheets

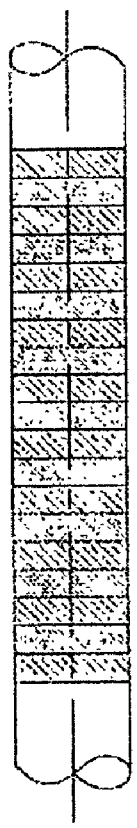
FIG. 4A
FIG. 4B
FIG. 4C

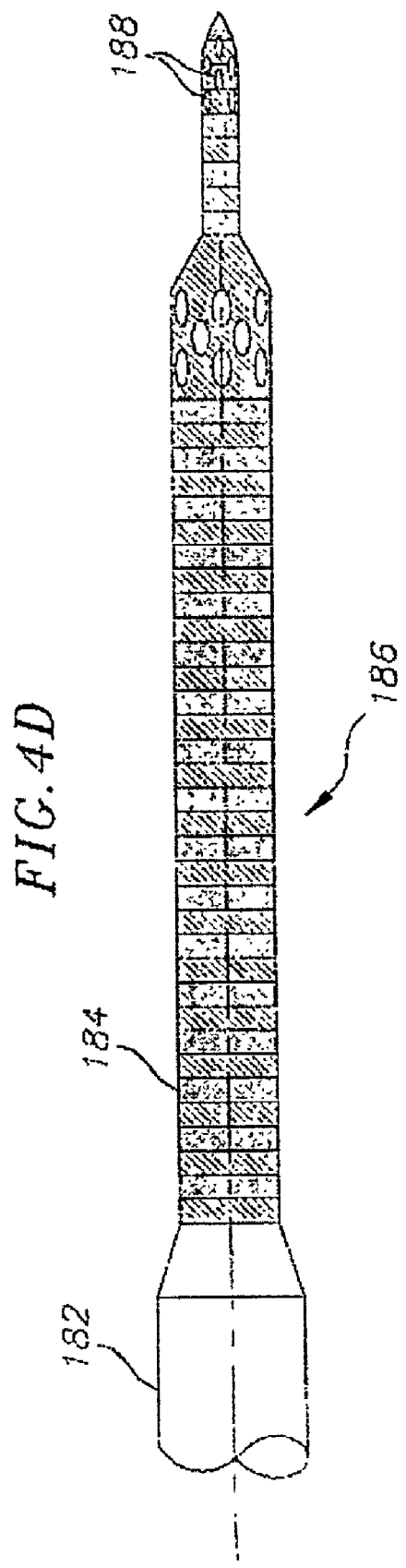

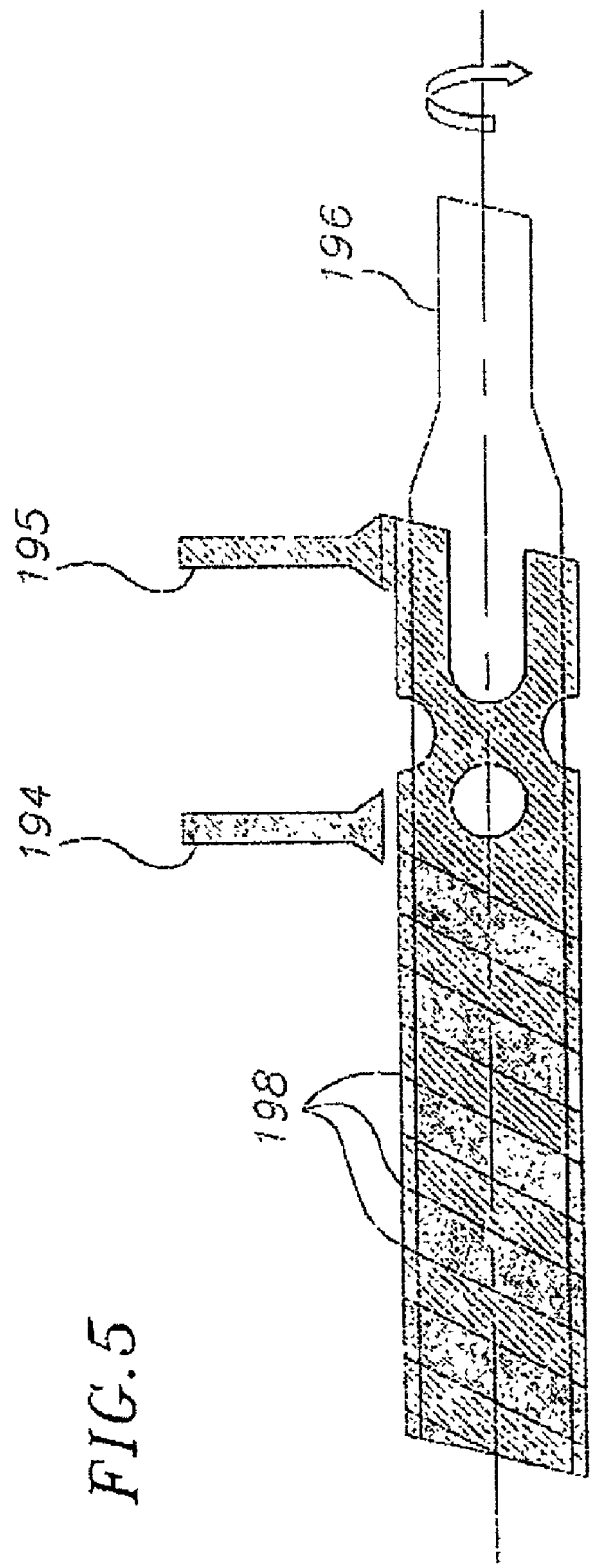

DISPENSE MOLDING METHOD AND APPARATUS FOR MANUFACTURING CANNULAE

RELATED APPLICATIONS

This application is a continuation-in-part application of patent application Ser. No. 10/172,668, entitled "Wave Molding Method and Apparatus for Manufacturing Cannulae," filed Jun. 14, 2002, which is specifically incorporated by reference herein.

FIELD OF THE INVENTION

The present invention is related generally to manufacturing cannulae and more specifically to a dispense molding process for manufacturing various sizes and configurations of cannulae.

BACKGROUND OF THE INVENTION

A cannula is basically a small tube made for insertion into a body cavity or into a duct or vessel for infusion, draining or monitoring. Cannulae also include various types of specialized tubing that are used in the surgical field to transport blood from the heart to a cardiopulmonary pump and oxygenator, and to return the blood to the circulatory system. While there are standard configurations of cannulae, many are custom-designed to suit the individual surgeon's requirements. Leading corporations produce more than 1,200 types of cannulae and accessories to facilitate cardiopulmonary bypass. More recent developments include a line of cannulae to facilitate vacuum-assisted venous drainage during cardiopulmonary bypass and dispersion aortic cannulae, which are used to reduce the pressure of blood flow returning to the body through the aorta.

Cannulae and catheters are manufactured by utilizing various different processes. U.S. Pat. Nos. 5,537,729, 5,722,395, and 5,785,998 describe some of the current manufacturing processes that may be utilized in producing cannulae and catheters and are incorporated herein by reference. U.S. Pat. No. 3,802,908 issued to Emmons discloses a process for forming a multi-layer resinous coating on the outer surfaces of pipe by applying flowable heat softened resinous material directly to the external surface of a rotating cylindrical pipe at ambient temperature. U.S. Pat. Nos. 5,537,729, 5,722,395, and 5,785,998 issued to Kolobow disclose a method of making ultra thin walled wire reinforced endotracheal tubing. Kolobow discloses thin walled tubing manufactured of a polymeric material having a spring wire material incorporated therewith. Utilization of the spring wire material in combination with the polymeric material results in reduced wall thickness, which decreases the resistance to airflow through the endotracheal tubing. The endotracheal tubing is made by depositing a dissolvable polymeric material on a rotating mandrel in successive layers. A spring material is also applied around the mandrel to produce the ultra thin walled wire reinforced endotracheal tubing. By controlling the rate of deposition of the polymeric material along the length of the mandrel, different wall thicknesses of tubing may be achieved.

During an extrusion process, polymer material is forced through a die. Almost any solid or hollow cross-section may be produced by utilizing the extrusion process. After a first layer is applied over the mandrel utilizing the extrusion process, a wire is wrapped around the first layer. Once wrapped with the wire, a second layer is extruded over the wire to produce a cannula that is wire-reinforced. Once the plastic reinforced tube is extruded, it is stripped from the mandrel, and cut in a desired length. Additional pieces, depending on the specific design of the cannula, are molded, welded, or connected to the plastic reinforced tube to create a cannula. These various process steps can be very expensive because of small lots of production and varying sizes of cannulae. Most of the cost savings with the extrusion process come from being able to run thousands of feet at a time.

U.S. Pat. No. 6,030,371 issued to Pursley discloses an apparatus and method for nonextrusion manufacturing of catheters having a simple or complex configuration. A polymer material in a particulate preform is applied in a layer over an outer surface of a core member. By applying the polymer material in a particulate preform, a composition of the polymer material can be varied continuously as it is being applied to provide a variable hardness over the length of the catheter. A fibrous reinforcement can be used having a constant or variable pitch and a constant or variable number of fibers and fiber types. Sensors can be easily placed in a wall of the catheter as the catheter is being fabricated, thereby allowing more sensors to be used without placing conductors in the lumen of the catheter. Deflection passages can be provided in a wall of the catheter for inserting a wire to deflect the catheter. The polymer material can be heated into molten form as it is being applied, or the core mandrel or liner can be heated to cause the polymer material to consolidate upon impact. A mandrel in the preferred embodiment is rotated about its longitudinal axis while a spray head and filament winding head traverse the length of the mandrel and apply polymer material and filament, respectively. Other arrangements can also be used, including a spray head and filament winding head that rotate about a continuous core mandrel, and a fluidized bed or other container into which a heated core mandrel is immersed. A plurality of mandrels can be placed side-by-side to form a multiple lumen tubing.

A dipping process is commonly used with silicon and other types of thermal set material. U.S. Pat. No. 5,885,251 issued to Luther discloses a dipping process associated with producing a catheter and is incorporated herein by reference. The catheter is formed by a sequential mandrel dip process. More particularly, a rigid tip portion may be formed by dipping a mandrel into a solubilized softenable material and allowing the softenable material to dry on the mandrel. The softenable material is preferably hydrated from the mandrel and the desired length for the distal tip portion is cut off. This distal portion is then applied to and dried on a secondary dipping mandrel and a length of flexible catheter is inserted over the mandrel such that the catheter abuts the softenable distal portion. The softenable portion and the portion of flexible catheter are then dipped into a liquid polymer such that the two portions are solvent welded together and an outer layer of polymer is deposited thereover. Thus a contiguous assembly is formed by bonding the softenable material to the distal end of the flexible catheter. The assembly is then allowed to dry and the dipped softenable tip portion is trimmed to exhibit a profile that facilitates insertion into a patient. The mandrel is subsequently removed from the assembly of the catheter and the softenable portion such that a continuous lumen is formed within both portions. A needle cannula is then inserted through the wall of the catheter and extended axially through the length of the catheter such that its sharp tip extends outwardly beyond the softenable end of the catheter.

Although the dipping process may be desirable in certain situations, dipping is sometimes not a desirable option for cannulae manufacturing because of excessive cost, extended process cycle time, many secondary steps to make a final product, and a need for on-going monitoring and adjustments during the manufacturing process. These variables and additional process steps significantly increase the cost of the product.

SUMMARY OF THE INVENTION

The present invention provides a method for making a cannula utilizing dispense molding. The method includes one or more of the following steps. Preheating a mandrel, rotating the mandrel, dispensing polymer material around the mandrel through one or more nozzles thereby forming a tubular structure, curing the polymer material and stripping the cured polymer material.

In another embodiment, a method of making a cannula utilizing dispense molding includes providing at least one dispense nozzle that dispenses a polymer material, providing a mandrel, moving at least one of the mandrel and the at least one dispense nozzle relative to one another to produce an alternating pattern of polymer material along a longitudinal axis of the mandrel to form a tubular structure, and removing the tubular structure from the mandrel. The method may further include pre-heating the mandrel.

In another embodiment, the method includes rotating the mandrel around the longitudinal axis of the mandrel while the at least one dispense nozzle dispenses polymer material onto the mandrel to form the tubular structure. The method further includes rotating the mandrel at a pre-determined speed in contact with the dispensed polymer material for a pre-determined period of time. In a further embodiment, the method includes curing the polymer material mandrel prior to removing the tubular structure from the mandrel. The method further provides creating holes at pre-determined locations in the tubular structure by controlling a flow of the polymer material that is being dispensed from the nozzle.

The method further permits the production of tubular structures with varied dimensions and strengths by regulating the type of the nozzle, the type of the mandrel, the rotating step, the preheating step, and the selection of the polymer materials.

In another embodiment, an apparatus for manufacturing a cannula utilizing a dispense molding method is disclosed. The apparatus includes a plurality of reservoirs, each containing a polymer material solution, a mandrel, a plurality of nozzles, a pump to force the polymer material up through an opening of each nozzle to dispense the polymer material solution from each nozzle, a motor to rotate the mandrel, and an actuator to traverse each of the plurality of nozzles, whereby each nozzle forces the polymer material solution around a selected section of the mandrel in an alternate pattern. Alternatively, or in addition to the actuator, a platform for the reservoir(s) and/or nozzle(s) is provided to move the dispensing of the material along the mandrel that is being rotated around its longitudinal axis.

The apparatus further includes a heater to apply heat to the mandrel at predetermined stages of manufacturing to cure the polymer material to produce a tubular structure. The heater is further configured to pre-heat the mandrel, and to cure a final coat over the mandrel by utilizing an induction coil. The apparatus may include other methods known in the art instead of the induction coil to apply heat. The polymer material solution utilized in the apparatus may be plastisol, silicone, organisol, ridgisol, or urethane. Depending on the type of the material selected, preheat or cure may not be required because the solvent is evaporated leaving polymer as a desired layer.

In yet another embodiment, the apparatus is configured to produce a cannula having two or more sections with different properties. In such a situation, the other components of the apparatus, such as a number of nozzles, a number of reservoirs, an actuator and a type of polymer material solutions are modified depending on the type of the cannula that is being produced.

BRIEF DESCRIPTION OF THE DRAWINGS

The invention is best understood from the following detailed description when read in conjunction with the accompanying drawings. Like numerals denote like features throughout the specification and drawings. Included are the following figures:

FIGS. 4A through 4D are side views of cannula showing different patterns created by dispense molding processes of the present invention.

FIG. 5 is a schematic representation of an apparatus for use in the present invention depicting multiple nozzles dispensing polymer material in a spiral pattern on the mandrel and to dispense polymer material to create holes.

DETAILED DESCRIPTION

The present invention relates to an apparatus and a method for manufacturing cannulae and more specifically to a dispense molding process for manufacturing various sizes and configurations of cannulae that reduces unit cost and improves performance of cannulae.

Figure 1:
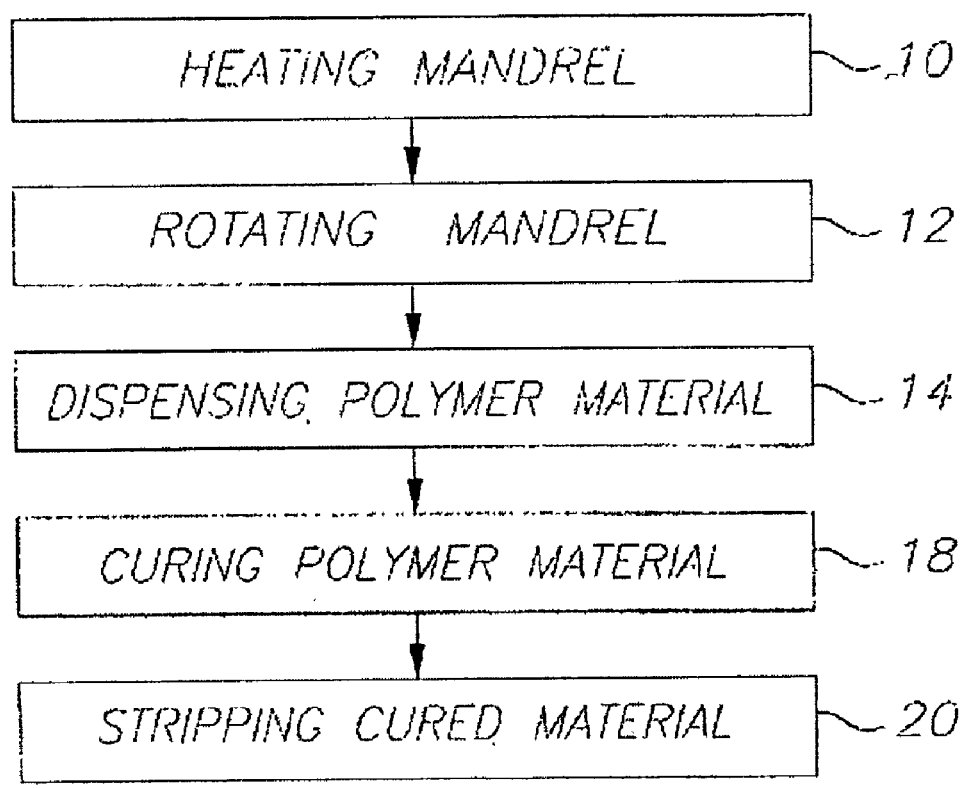
FIG. 1 is a flowchart of manufacturing steps for a dispense molding embodiment of the present invention.

With reference to FIG. 1, a method of manufacturing cannulae using a dispense molding process includes pre-heating a mandrel (step 10), rotating the mandrel (step 12), dispensing polymer material onto the rotating mandrel (step 14), curing the polymer material (step 18) and stripping the cured polymer material from the mandrel (step 20). In one embodiment of the method, the pre-heating, rotating, curing and stripping steps, are all accomplished in the same manner as described in a related application entitled Wave Molding Method and Apparatus for Manufacturing Cannulae, Ser. No. 10/172,668, filed Jun. 14, 2002, by Ross Bartholomew, incorporated by reference herein.

In another embodiment of the invention, a dispense molding method includes providing at least one dispense nozzle that dispenses a polymer material, providing a mandrel, moving at least one of the mandrel and the at least one dispense nozzle relative to one another to produce an alternating pattern of polymer material along a longitudinal axis of the mandrel to form a tubular structure, and removing the tubular structure from the mandrel.

Figure 2:
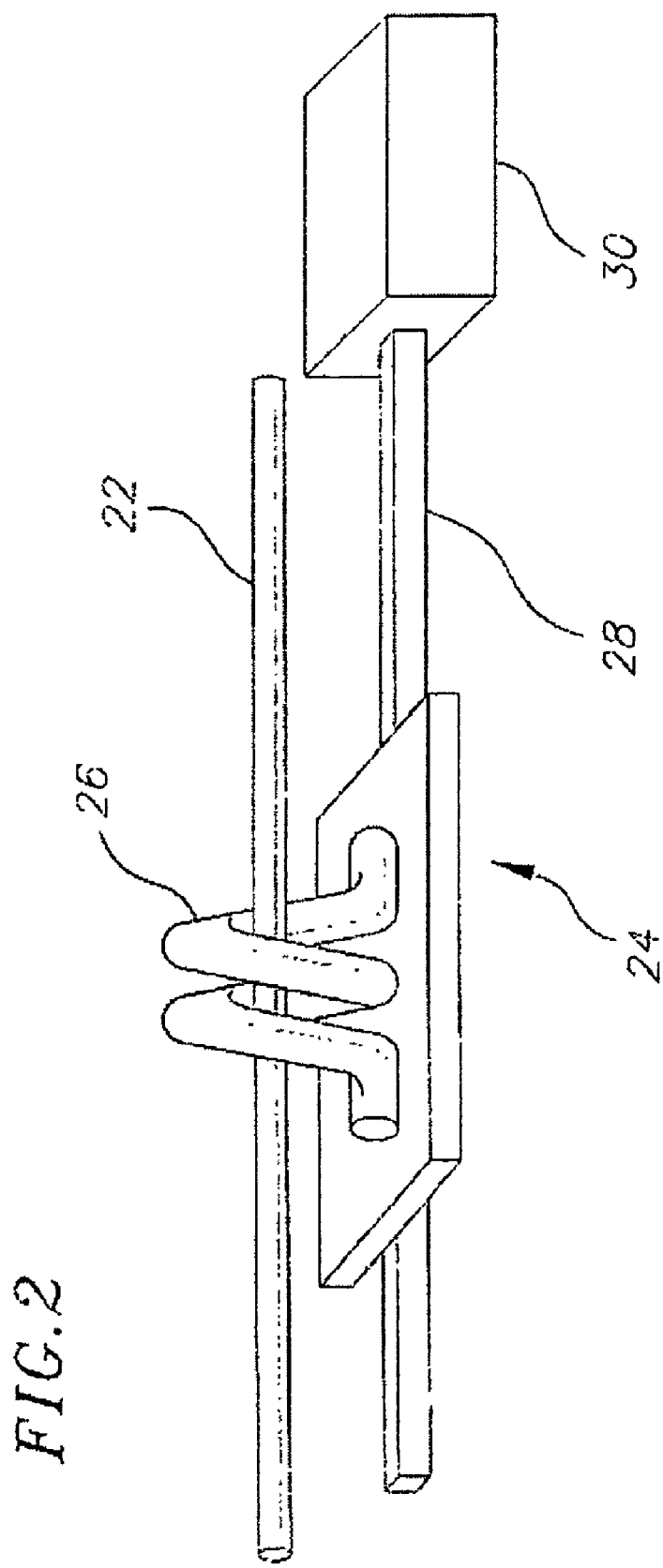
FIG. 2 is a schematic representation of a heater for use in the present invention.

With reference to FIG. 2, an elongated mandrel 22 is heated using a heating apparatus 24 that includes an induction coil 26 mounted to a rail 28. The rail is moveable to permit the induction coil to move along the mandrel to heat selected areas along the length of the mandrel. The induction coil and rail are controlled by a controller 30 that is programmed as desired to control the movement of the rail as well as the power output of the induction coil. When the induction coil passes over the mandrel, the mandrel heats up depending on the power output of the coil.

Instead of the induction coil, the heating apparatus may be any other commercially available apparatus to supply heat to the mandrel, for example, a radiant heater, a conduction heater, or a convection heater. It will be appreciated by those skilled in the art that instead of moving the heating apparatus along the mandrel, a mechanism can be provided to move the mandrel along the heating mechanism and heating means may be provided with no movement of either mandrel or heater.

Figure 3:
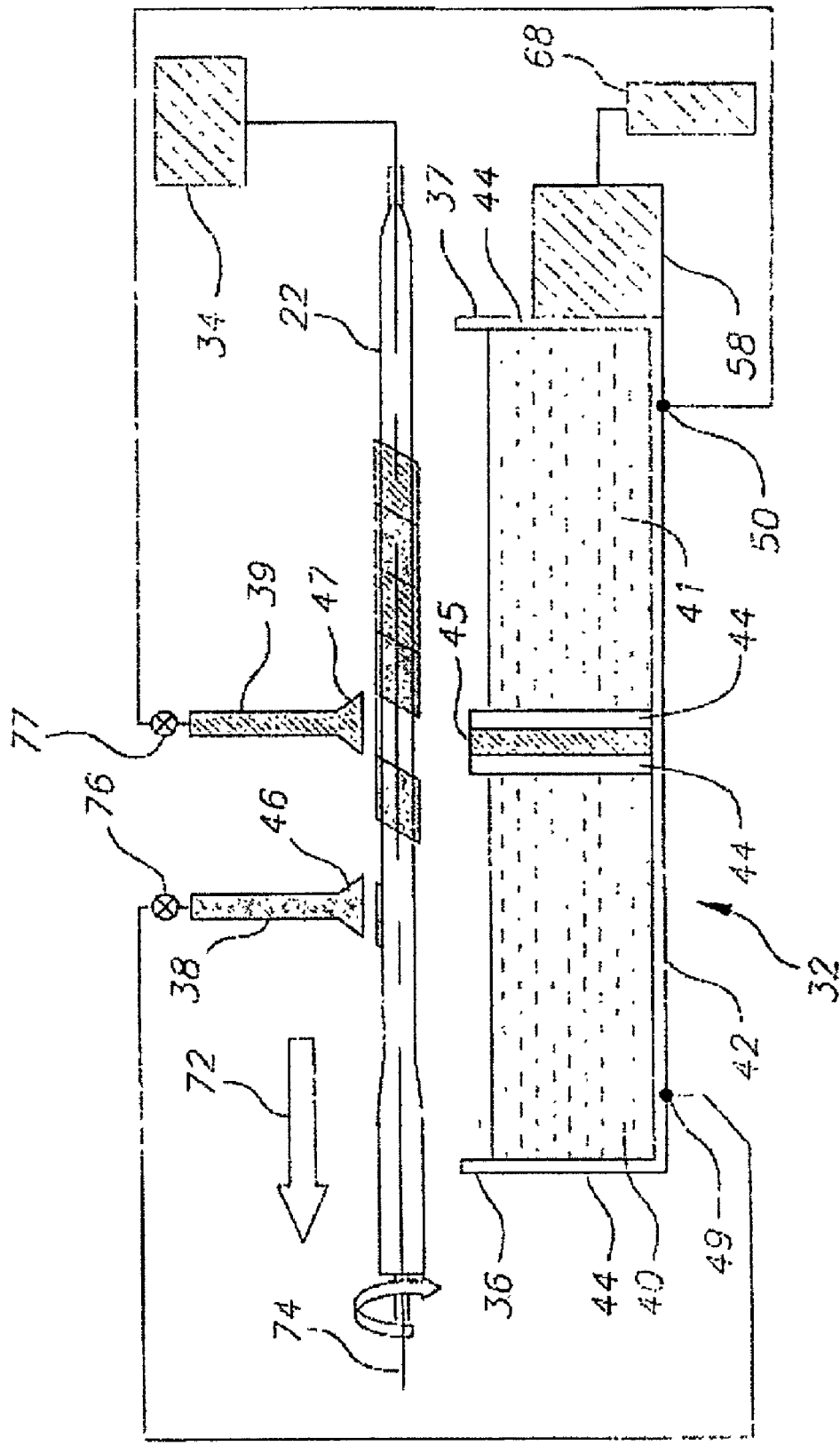
FIG. 3 is a schematic representation of an embodiment of an apparatus for use in the present invention depicting multiple nozzles dispensing polymer material in a spiral pattern on the mandrel.

With reference to FIG. 3, a dispense molding apparatus 32, includes a lathe 34 for rotating the mandrel, a plurality of reservoirs 36 and 37, and a plurality of nozzles 38 and 39 for receiving polymer material from the reservoirs 36 and 37 respectively. The nozzles 38, 39 dispense different polymer materials, e.g., having different durometers from the nozzles, onto the mandrel 22. The nozzles do not spray the polymer materials. Instead, they dispense the polymer materials onto the mandrels in a continuous layer. The lathe 34 is indicated schematically because mechanisms for rotating the mandrel are well known in the art.

Reservoirs 36, 37 are any suitable containers for holding a volume of polymer material 40, 41 to be used to form the cannulae. Each reservoir 36, 37 includes a base 42 and a plurality of walls 44. The reservoirs 36, 37 are separated by a middle wall 45. In one embodiment, instead of utilizing one reservoir with two compartments, two separate stand-alone reservoirs to supply two different types of polymer materials may be utilized. If desired, each reservoir 36, 37 also includes an independent heater (not shown) to maintain the polymer materials in the reservoirs at a pre-determined temperature depending on the type of the application. For example, an independent heater or heaters (not shown) can be mounted underneath the reservoirs to provide sufficient heat to the reservoirs to maintain the polymer material at a constant temperature for process consistency. Alternatively, or in addition to the heater, a cooling system (not shown) can be provided to maintain the reservoirs at a constant temperature for process consistency.

The nozzles 38 and 39 are mounted outside the reservoirs and have openings 46 and 47 respectively. Openings 49 and 50 are provided in the reservoirs to supply polymer material from the two reservoirs 36 and 37 to the nozzles 38 and 39. The polymer material is dispensed from the nozzles onto the mandrel to produce an alternating, e.g. spiral, pattern along a longitudinal axis of the mandrel. A metering pump, shown schematically at 58, pumps the polymer materials up through the nozzles 38 and 39 to dispense the polymer materials out of the openings 46 and 47 of the nozzles.

In one embodiment, the nozzles 38 and 39 create a side by side spiral strip as the nozzles traverse in the direction 72. The mandrel 22 may or may not be preheated, or just preheated in selected sections based on the application. The mandrel 22 rotates on its horizontal axis and the nozzles 38 and 39 move horizontally over the mandrel to coat the mandrel with the desired features, dimensions/configuration of the finished cannulae.

Relative movement between the rotating mandrel and the nozzles is required to bring the mandrel into contact with the polymer materials that are being dispensed from the nozzles. Such a mechanism for moving the mandrel, or a plurality of mandrels, and/or for moving the nozzles, are readily designed by those skilled in the art.

The polymer materials used to produce cannulae can be any suitable materials which have a liquid state while contained in the reservoir of the dispense molding apparatus and yet adhere to a mandrel when dispensed onto the mandrel by the passing nozzle. Preferably, a plastisol, such as polyvinyl chloride, having one or more of the following properties is used: flexible, clear/transparent, biocompatible, non-DEHP/DOP, has a durometer range of 60 Shore A to 60 Shore D, and/or is stable of over time (no discolorization or plastizer leaching). Other polymer material solutions such as organisol, silicone, ridgisol, and urethanes are also believed to be suitable.

A controller 68 is provided for the pump 58 to control the pressure and the quantity of the polymer materials. Two separate check valves 76 and 77 are provided to facilitate the dispensing of the polymer materials. The controller also can control the lathe for rotation of the mandrel and any transporting device that provides the relative movement between the mandrel and the nozzles. The controller can also be connected to the heater for the reservoir and the heater for the mandrel to regulate temperature. Such a controller can be readily designed by those skilled in the art taking into consideration the size, shape, and physical characteristics of the cannulae desired to be manufactured. In one embodiment, instead of one controller and one pump, multiple controllers with multiple pumps may be utilized depending on the complexity of the apparatus.

A method of making a cannula by dispense molding includes preheating the mandrel 22 utilizing the induction heating coil 26 (FIG. 2). When the induction heating coil passes over the mandrel, the mandrel heats up depending on the amount of current that is passed through the coil. The process allows the mandrel to be preheated in a relatively short period of time. As noted earlier, instead of moving the heater, the mandrel can be moved with respect to the heater. Furthermore, depending on the properties of the polymer material, no preheating step may be needed.

The metering pump 58 applies sufficient pressure to supply the polymer materials from the reservoirs 36, 37 to the nozzles 38, 39 and out of the openings 46, 47 of the nozzles to deposit a layer of polymer materials onto the rotating mandrel, which is rotated at a predetermined speed depending on the wall thickness desired for the cannula to be produced. The mandrel and the nozzles are moved relative to each other to place the mandrel in contact with the polymer materials over a predetermined length of the mandrel for a predetermined time period.

The nozzles 38, 39 are preferably arranged relative to each other such that the polymer materials from the reservoirs form an alternating spiral pattern onto the mandrel to ensure that the two adjoining sections of cannulae are fused together to form a seamless joint. Even though the polymer material solutions deposited around the mandrel may be different in hardness and/or color, the basic characteristics of the polymer material solutions are the same. Therefore, the deposited polymer material solutions around the mandrel in the alternating pattern, once cured, are fused together forming a seamless cannula. In one embodiment, a cannula with different hole patterns is created by controlling the flow of the polymer material that is being dispensed through one nozzle.

After the polymer material is dispensed onto the rotating mandrel, the polymer material that is adhered to the mandrel is cured. In one embodiment, the curing is accomplished utilizing the heater depicted in FIG. 2. Alternatively, the curing may include simply allowing sufficient time for the polymer material to harden. In some cases, depending on the properties of the polymer material, curing is not required. The cannula is then stripped from the mandrel by methods known in the art, such as by forcing compressed air between the mandrel and the cannula, which slightly expands the cannula so that it can be slid off the mandrel. In another embodiment, additional reservoirs and multiple nozzles may be used to permit application of additional polymer materials having different properties than the first two polymer materials to manufacture the cannulae with multiple varying properties along their length.

The dimensions of the tubular structure that are produced are varied by regulating at least one of the nozzle, the mandrel, the speed of the motor, the speed of the actuator, thermal energy of the mandrel, and the selection of the polymer material solution. The quality, type and grade of the polymer material are also factors to be considered based on the type and the application of the cannula. It is believed that known motion control systems could be adapted to produce cannulae having the desired characteristics. In addition, nozzles could be programmed to alternately turn on/off as desired to achieve the desired pattern.

For areas of the cannulae having an opening for drainage or perfusion, these areas are typically hardened by utilizing higher hardness polymer, or additional hardening steps. This ensures that these areas retain sufficient rigidity. Furthermore, during certain medical procedures, some of the areas of the cannula may be clamped. Areas that are clamped are typically not hardened. Therefore, it is necessary to have different wall thicknesses or hardnesses to support a specific area of the cannula based on the functionality requirement. The present invention allows the production of a cannula with different wall thicknesses and different hardnesses within the cannula—all in a single piece product without any bonds, or welds used for assembly. The process further allows production of cannulae with a thinner wall or a small outer diameter for a given inner diameter at substantially less cost than other traditional manufacturing processes such as extrusion and dipping.

With reference to FIGS. 4A and 4D, cannulae having different properties along their length may be made by controlling the relative movement of the nozzle and mandrel, controlling mandrel rotation and position, and controlling nozzle size, position and duration of dispense time. For example, the pattern 120 in FIG. 4 is made by dispensing polymer from two nozzles simultaneously while the mandrel is roating at a fixed location. After one portion of the mandrel is coated, the dispensing is stopped, and the mandrel is translated to an adjacent location, wherein dispensing begins again to produce coatings of materials adjacent to the coatings previously produced. This results in an alternating pattern of rings. If one dispenser supplies a hard durometer material and the other supplies a soft durometer material, then a reinforced cannula structure is produced.

The spiral pattern 140 of FIG. 4B is produced by simply translating a rotating mandrel adjacent the two nozzles. If hard and soft polymer materials are used, the result is a cannula having a springlike reinforcement.

With reference to FIG. 4C, longer sections 160 of one type of coating may be produced by leaving one nozzle on and turning the other nozzle off, then moving the mandrel or nozzle to achieve the desired length of tube made from the desired polymer material.

A cannula having varying diameters 182, 184, alternating patterns 186, and holes 188 may also be produced, as shown in FIG. 4D. To produce the holes, one nozzle is turned off intermittently during rotation and/or during translation of the mandrel to produce the portion of the cannula that defines the desired hole or holes. Alternatively, the nozzle is left on and moved around the mandrel to define the desired hole or holes.

With reference to FIG. 5, a pair of nozzles 194, 195 are shown for coating a mandrel 196 in an alternating, spiral pattern 198 beginning at one end and wherein the other end of the mandrel has holes and a slot formed in it due to the dispensing operation of one nozzle. A combination of two or more polymer materials are dispensed on to the preheated mandrel in patterns to create reinforced structures in the cannulae. This process eliminates a need for hole punching operations which is normally needed to finish the cannula. In one embodiment, the dimensions are controlled by the size of the nozzle outlet, the polymer material dispense rate and the relative movement of the nozzle and the mandrel. Different colors of polymer material could be used to create features such as depth lines, orientation marks, product codes, and serialization numbers.

The dispense molding process can eliminate a need for a spring wire or a reinforcing sleeve and can further eliminate the printing, cutting, and hole punching operations. Many products could come off the machine ready to package with a very short cycle time. The process further provides tight controls over dimensions and properties. Additionally, the process helps reduce the polymer material waste thereby directly reducing the product material and labor cost. The dispense molding process does not require acetate treatment for selective hardening.

Figure 6:
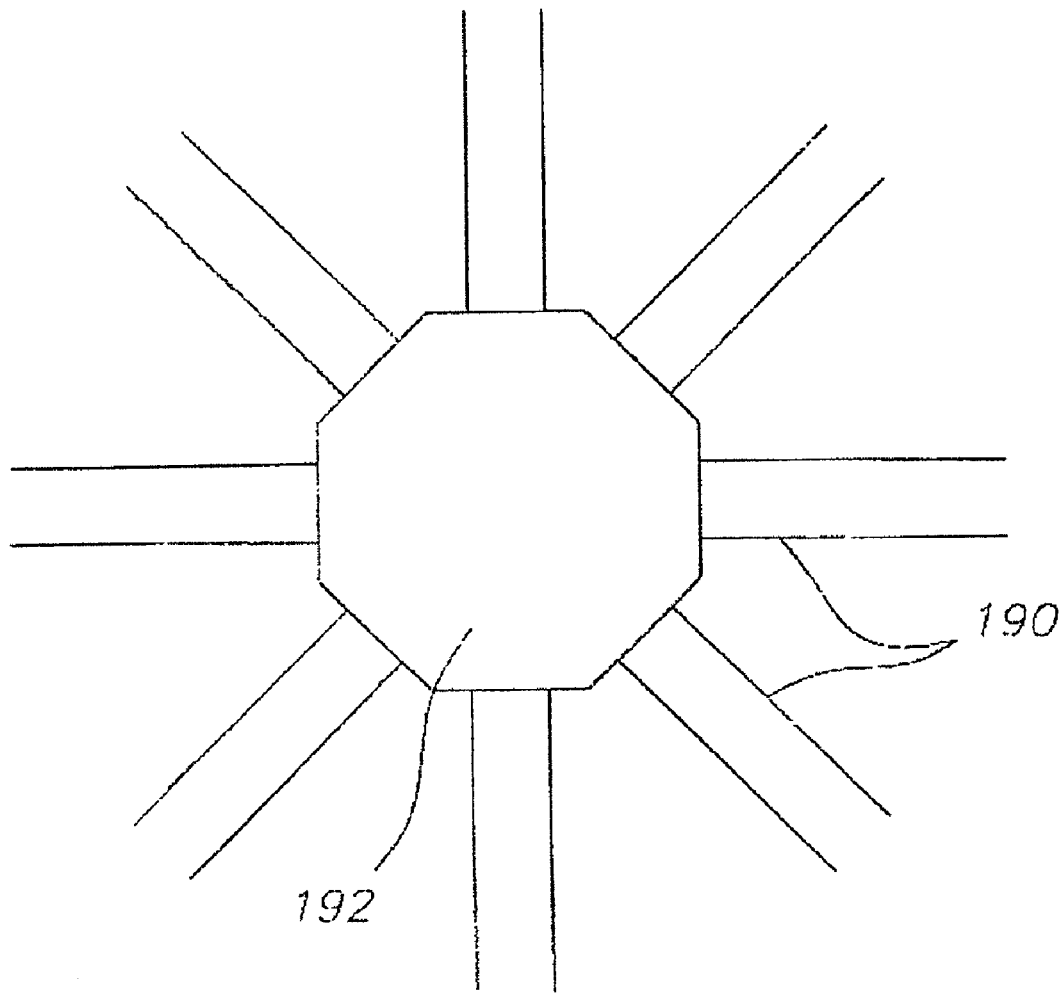
FIG. 6 is a schematic of an automated system for producing multiple cannulae through the dispense molding process of the present invention.

With reference to FIG. 6, an automated system is schematically shown wherein a plurality of rotatable mandrels 190 are mounted to a rotatable center post 192 that would carry the mandrels through the various processes. For dispensing, the mandrels would rotate on their horizontal axes, while a nozzle or nozzles would move horizontally over each mandrel to coat the mandrels and produce the desired features, dimensions or configurations. Although one automated system is described here, alternative systems would be readily developed by those skilled in the art.

It will, of course, be understood that modifications to the present preferred embodiment will be apparent to those skilled in the art. Consequently, the scope of the present invention should not be limited by the particular embodiments discussed above, but should be defined only by the claims set forth below and equivalents thereof.

What is claimed is:

1. A method of making a cannula utilizing dispense molding, the method comprising:

supplying polymer material to at least one dispense nozzle;

dispensing polymer material from the at least one dispense nozzle onto a mandrel to form a tubular structure having a wall on the mandrel; and removing the tubular structure from the mandrel;

wherein dispensing includes moving at least one of the mandrel and the at least one dispense nozzle relative to one another and dispensing polymer material from a first dispense nozzle of the at least one dispense nozzle along an axially extending portion of the mandrel, leaving at least a part of the axially extending portion of the mandrel uncovered with polymer material from the first dispense nozzle to form an opening through the wall of the tubular structure.

2. The method of claim 1, wherein the opening is one of a hole or a slot.

3. A method of making a cannula utilizing dispense molding, the method comprising:
supplying polymer material to at least one dispense nozzle;
dispensing polymer material from the at least one dispense nozzle onto a mandrel to form a tubular structure on the mandrel; and
removing the tubular structure from the mandrel;
wherein dispensing includes moving at least one of the mandrel and the at least one dispense nozzle relative to one another and dispensing at least one continuous layer of polymer material from a first dispense nozzle of the at least one dispense nozzle along an axially extending portion of the mandrel, leaving at least a part of the axially extending portion of the mandrel uncovered with polymer material from the first dispense nozzle;
wherein the at least one dispense nozzle includes a second dispense nozzle that dispenses polymer material, and wherein dispensing includes moving the mandrel and the dispense nozzles relative to one another and dispensing at least one continuous layer of polymer material from the second dispense nozzle along an axially extending portion of the mandrel, leaving at least a part of the axially extending portion of the mandrel uncovered with polymer material from the second dispense nozzle.

4. The method of claim 3, wherein polymer material from the first dispense nozzle and polymer material from the second dispense nozzle have different properties.

5. The method of claim 4, wherein polymer material dispensed from the first and second dispense nozzles results in an alternating pattern of polymer material along a longitudinal axis of the mandrel.

6. The method of claim 5, wherein the alternating pattern is adjacent, alternating rings of polymer material from the first dispense nozzle and polymer material from the second dispense nozzle.

7. The method of claim 5, wherein the alternating pattern is an alternating spiral pattern of polymer material from the first dispense nozzle and adjacent polymer material from the second dispense nozzle.

8. The method of claim 3 further comprising pre-heating the mandrel.

9. The method of claim 3 further comprising rotating the mandrel around its longitudinal axis while the at least one dispense nozzle dispenses polymer material onto the mandrel.

10. The method of claim 3 wherein the cannula is manufactured utilizing at least one of plastisol, silicon, ridgisol, organisol, and urethanes.

11. A method of making a cannula utilizing dispense molding, said method comprising:
providing a plurality of reservoirs each containing polymer material;
providing a plurality of nozzles each dispensing polymer material from a respective one of the plurality of reservoirs;
moving a mandrel relative to the plurality of nozzles and dispensing polymer material onto the mandrel from the plurality of nozzles such that dispensed polymer material creates a tubular structure around the mandrel wherein polymer material dispensed from the plurality of nozzles results in an alternating pattern of polymer material along a longitudinal axis of the mandrel, wherein the alternating pattern of polymer material along the longitudinal axis of the mandrel is an alternating pattern of polymer material dispensed from a first dispense nozzle of the plurality of nozzles and polymer material dispensed from a second dispense nozzle of the plurality of nozzles;
curing the tubular structure; and
removing the tubular structure from the mandrel.

12. The method of claim 11 further comprising creating holes in a wall of the tubular structure at pre-determined locations by controlling the flow of the dispensed polymer material.

13. The method of claim 11, wherein polymer material from the first dispense nozzle of the plurality of nozzles and polymer material from the second dispense nozzle of the plurality of nozzles have different properties.

14. The method of claim 13, wherein the alternating pattern is adjacent, alternating rings of polymer material from the first dispense nozzle and polymer material from the second dispense nozzle.

15. The method of claim 13, wherein the alternating pattern is an alternating spiral pattern of polymer material from the first dispense nozzle and adjacent polymer material from the second dispense nozzle.

16. A method of making a cannula utilizing dispense molding, said method comprising:
providing a plurality of reservoirs each containing polymer material;
providing a plurality of nozzles each dispensing polymer material from a respective one of the plurality of reservoirs;
moving a mandrel relative to the plurality of nozzles and dispensing polymer material onto the mandrel from the plurality of nozzles such that dispensed polymer material creates a tubular structure around the mandrel wherein polymer material dispensed from the plurality of nozzles results in an alternating pattern of polymer material along a longitudinal axis of the mandrel;
curing the tubular structure; and
removing the tubular structure from the mandrel;
wherein polymer material from a first dispense nozzle of the plurality of nozzles is a high durometer polymer material and polymer material from a second dispense nozzle of the plurality of nozzles is a low durometer polymer material; wherein the alternating pattern of polymer material along the longitudinal axis of the mandrel is an alternating pattern of the high durometer polymer material from the first dispense nozzle and the low durometer polymer material from the second dispense nozzle.

* * * * *